US009414779B2

(12) United States Patent
Kanevsky et al.

(10) Patent No.: US 9,414,779 B2
(45) Date of Patent: *Aug. 16, 2016

(54) ELECTRONIC COMMUNICATION WARNING AND MODIFICATION

(75) Inventors: Dimitri Kanevsky, Ossining, NY (US); James R. Kozloski, New Fairfield, CT (US); Clifford A. Pickover, Yorktown Heights, NY (US); Tara N Sainath, New York, NY (US)

(73) Assignee: International Business Machines Corporation, Armonk, NY (US)

( * ) Notice: Subject to any disclaimer, the term of this patent is extended or adjusted under 35 U.S.C. 154(b) by 424 days.

This patent is subject to a terminal disclaimer.

(21) Appl. No.: 13/611,825

(22) Filed: Sep. 12, 2012

(65) Prior Publication Data

US 2014/0074945 A1 Mar. 13, 2014

Related U.S. Application Data

(63) Continuation of application No. 13/611,406, filed on Sep. 12, 2012.

(51) Int. Cl.
  G06F 15/16 (2006.01)
  A61B 5/16 (2006.01)
  G06Q 10/10 (2012.01)
  G06Q 50/00 (2012.01)

(52) U.S. Cl.
  CPC .............. A61B 5/165 (2013.01); G06Q 10/107 (2013.01); G06Q 50/01 (2013.01)

(58) Field of Classification Search
  CPC .............. G06Q 10/107; H04L 12/585; H04L 29/08072; G10L 25/63
  USPC ............ 709/206, 207; 715/752, 753; 707/100
  See application file for complete search history.

(56) References Cited

U.S. PATENT DOCUMENTS

| | | | |
|---|---|---|---|
| 7,289,949 B2 | 10/2007 | Warner et al. | |
| 7,983,910 B2 | 7/2011 | Subramanian et al. | |
| 8,041,344 B1* | 10/2011 | Coughlan | H04L 12/585 455/414.1 |
| 8,109,874 B2* | 2/2012 | Kong | A61B 5/0205 128/920 |
| 8,209,385 B2 | 6/2012 | Partaker et al. | |
| 8,239,774 B2 | 8/2012 | Gandhi et al. | |
| 2003/0069936 A1* | 4/2003 | Warner | G06F 17/271 709/206 |
| 2004/0117212 A1* | 6/2004 | Kong | G06Q 50/22 705/2 |
| 2005/0198125 A1 | 9/2005 | Macleod Beck et al. | |
| 2006/0203992 A1* | 9/2006 | Kim | 379/265.06 |
| 2006/0253784 A1 | 11/2006 | Bower et al. | |
| 2008/0043942 A1* | 2/2008 | Cardona | H04L 12/583 379/88.18 |

(Continued)

OTHER PUBLICATIONS

Rosen, 18 Common Work E-mail Misktakes, on Careers (usnews.com), Jan. 18, 2011, pp. 1-2.

(Continued)

*Primary Examiner* — Aftab N. Khan
(74) *Attorney, Agent, or Firm* — Ryan, Mason & Lewis, LLP (57) ABSTRACT

A system and article of manufacture for electronic communication warning and modification include automatically detecting an emotional state of a sender of an electronic communication, encoding the detected emotional state of the sender, using input from at least one additional source, as metadata, embedding the metadata in the electronic communication to create an annotated version of the electronic communication, and transmitting the annotated version of the electronic communication to a recipient.

15 Claims, 2 Drawing Sheets

(56) References Cited

U.S. PATENT DOCUMENTS

| | | | | |
|---|---|---|---|---|
| 2008/0096532 | A1* | 4/2008 | Lyle | G06Q 10/107 |
| | | | | 455/412.1 |
| 2008/0320037 | A1 | 12/2008 | MacGuire et al. | |
| 2009/0002178 | A1 | 1/2009 | Guday et al. | |
| 2009/0144366 | A1 | 6/2009 | Lyle | |
| 2009/0157708 | A1* | 6/2009 | Bandini | H04L 12/585 |
| 2009/0164549 | A1* | 6/2009 | Jung | G06Q 30/02 |
| | | | | 709/201 |
| 2010/0049807 | A1 | 2/2010 | Thompson | |
| 2010/0082751 | A1* | 4/2010 | Meijer | G06F 15/16 |
| | | | | 709/206 |
| 2010/0145695 | A1* | 6/2010 | Jung | G10L 17/26 |
| | | | | 704/246 |
| 2010/0223581 | A1* | 9/2010 | Manolescu | G06Q 10/10 |
| | | | | 715/853 |
| 2011/0055334 | A1 | 3/2011 | Tivyan | |
| 2012/0272160 | A1* | 10/2012 | Spivack et al. | 715/752 |
| 2012/0284332 | A1* | 11/2012 | Pradeep et al. | 709/204 |
| 2013/0019187 | A1* | 1/2013 | Hind | H04L 65/4023 |
| | | | | 715/753 |
| 2013/0280682 | A1* | 10/2013 | Levine | G06Q 50/01 |
| | | | | 434/236 |
| 2014/0052792 | A1* | 2/2014 | Dunko | 709/206 |

OTHER PUBLICATIONS

Tschabitscher, How to Create an Email Signature in Outlook, About.com, downloaded Sep. 12, 2012, pp. 1-2.

ToneCheckTM, http://tonecheck.com, downloaded Sep. 12, 2012, pp. 1-2.

OPA, OPA Unveils Biometric and Eye Tracking Research to Assess the Effectiveness of New OPA Ad Units, Nov. 2, 2010, pp. 1-2.

Riga, Biometric Mouse Intelligent System for Student's Emotional and Examination Process Analysis, Jul. 15-17, 2009, Abstract.

Keyboard Biometrics Definition from PC Magazine Encyclopedia, downloaded Sep. 12, 2012, pp. 1-2.

Planet Pulse, Emotional Sensing Necklace Talks to Others . . . But in Gaudy Design or Sensory Communication? downloaded Sep. 12, 2012, pp. 1-4.

Calvalho et al., Preventing Information Leaks in Email, Proceedings of SIAM International Conference on Data Mining, SDM-07, 2007, pp. 68-77.

Sanchez et al., Conveying Mood and Emotion in Instant Messaging by Using a Two-Dimensional Model for Affective States, Proceedings of VII Brazilian Symposium on Human Factors in Computing Systems, IHC '06, 2006, pp. 66-72.

Balebako et al., Nudging Users Towards Privacy on Mobile Devices, ACM CHI Conference on Human Factors in Computing Systems, CHI 2011, May 7-12, 2011.

* cited by examiner

ELECTRONIC COMMUNICATION WARNING AND MODIFICATION

CROSS-REFERENCE TO RELATED APPLICATIONS

This application is a continuation of U.S. patent application Ser. No. 13/611,406, filed Sep. 12, 2012, and incorporated by reference herein.

FIELD OF THE INVENTION

Embodiments of the invention generally relate to information technology, and, more particularly, to electronic communication technology.

BACKGROUND

Mistakes involving inappropriate sending of messages, electronic and otherwise, are common. Typical forms of communication with which such situations arise can include email, instant messaging (IM), virtual worlds and/or online communities. Each such form of communication can present unique challenges in this regard.

For instance, email messages include a message header, which can contain information such as sender and recipient(s) email address(es), as well as a subject line header or title. Email messages also include a message body, which generally contains the sender-generated content of the message. The message body can additionally contain a signature, which contains text included (often automatically) to an e-mail message (often at the end of the message). A signature can include a sender's name as well as additional contact information pertaining to the sender. In some instances, a signature can also include user-chosen or user-generated content (text and/or images, generally limited to a brief amount).

Additionally, instant messaging (IM) enables real-time text- or image-based communication over a network (commonly the Internet) between two or more people using capable devices such as smart phones, personal computers, tablets, etc. Similarly, virtual worlds and various online communities provide for similar messaging capabilities to allow users to interact with each other in real-time.

Accordingly, opportunities can present themselves wherein a user of one of these example forms of electronic communication may transmit a message that the user, recipient or third-party might deem inappropriate. For example, a user of an email system may send an inappropriate or undesired email when he or she is angry. A user may also attach an inappropriate signature to an email while under a similar emotional state. As such, a need exists to provide means by which the likelihood of a user transmitting such communications is reduced.

SUMMARY

In one aspect of the present invention, techniques for electronic communication warning and modification are provided. An exemplary computer-implemented method for transmitting an electronic communication in annotated form based on a detected emotional state of a sender of the electronic communication can include steps of automatically detecting an emotional state of a sender of an electronic communication, encoding the detected emotional state of the sender, using input from at least one additional source, as metadata, embedding the metadata in the electronic communication to create an annotated version of the electronic communication, and transmitting the annotated version of the electronic communication to a recipient.

Another aspect of the invention relates to a method for automatically managing a transmission of an electronic communication based on an emotional state of a sender of the electronic communication can include steps of automatically detecting an emotional state of an author of an electronic communication, providing the author with a notification of the detected emotional state, delaying transmission of the electronic communication to a recipient by a pre-determined amount of time that is a function of the detected emotional state of the author, and deploying an action to facilitate modification and/or cancellation of the transmission of the electronic communication during said delay.

Yet another aspect of the invention or elements thereof can be implemented in the form of an article of manufacture tangibly embodying computer readable instructions which, when implemented, cause a computer to carry out a plurality of method steps, as described herein. Furthermore, another aspect of the invention or elements thereof can be implemented in the form of an apparatus including a memory and at least one processor that is coupled to the memory and operative to perform noted method steps. Yet further, another aspect of the invention or elements thereof can be implemented in the form of means for carrying out the method steps described herein, or elements thereof; the means can include (i) hardware module(s), (ii) software module(s), or (iii) a combination of hardware and software modules; any of (i)-(iii) implement the specific techniques set forth herein, and the software modules are stored in a tangible computer-readable storage medium (or multiple such media).

These and other objects, features and advantages of the present invention will become apparent from the following detailed description of illustrative embodiments thereof, which is to be read in connection with the accompanying drawings.

DETAILED DESCRIPTION

As described herein, an aspect of the present invention includes an electronic communication warning and modification system. At least one embodiment of the invention includes providing a system that automatically detects the emotional (or other) state of a user of a communication system (for example, an email system) and uses this information together with message context to reduce the likelihood of the user transmitting a communication inappropriately or with an inappropriate signature.

As further detailed herein, protective actions implemented by embodiments of the invention can include, for example, modifying, choosing, or removing the message signature block, sending the message to a designated reviewer, modifying the recipient of the email, issuing a warning to the sender, transmitting the message together with information about the user's emotional state when sending, and/or introducing a delay in sending the message. Note also that the emotional state of a sender can be automatically determined, sent, and conveyed to a recipient system that renders said state according to recipient preferences. By way of example, a special-needs recipient may wish to emphasize sender's emotional state in a computer-generated graphic.

Figure 1:
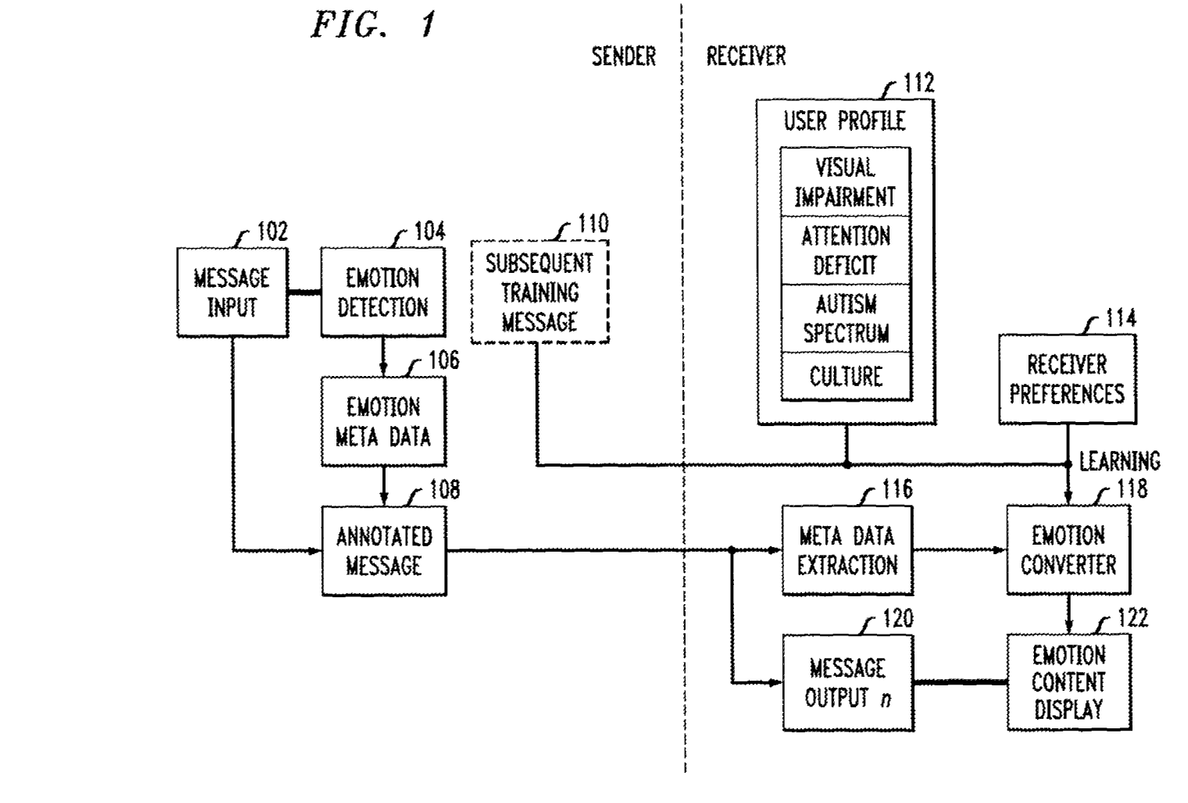
FIG. 1 is a block diagram illustrating an example embodiment, according to an aspect of the invention.

FIG. 1 is a block diagram illustrating an example embodiment, according to an aspect of the invention. By way of illustration, FIG. 1 depicts components and actions on a message sender side and components and actions on a message receiver side. Specifically, on the sender side, FIG. 1 depicts message input 102, an emotion detection module 104, emotion metadata 106, and an annotated message 108. At least one embodiment of the invention can also include a subsequent training message 110 on the sender side. A subsequent training message 110 can be sent by the originator/sender of a message or by a third party responsible for reviewing emotion metadata and/or annotations. The content of the training message 110 can include a revision to the original emotion metadata and/or annotations, and/or a corrective action to be taken by the emotion detection module 104 to enhance its ability to properly produce emotion metadata and/or annotations in subsequent messages, as in active learning systems.

On the receiver side, FIG. 1 depicts a user profile 112 (including information pertaining to possible user attributes such as visual impairment, attention deficit, autism spectrum, culture, etc.), a receiver preferences module 114, a meta data extraction module 116, an emotion converter module 118, message output 120 and an emotion content display 122.

As depicted in FIG. 1, the techniques detailed herein include detecting an emotion or emotional state of a user (via emotional detection module 104) in connection with a message (via message input 102), encoding the detected emotion or emotional state as a standard metadata descriptor 106, embedding the descriptor in an annotated version of the message 108, and transmitting the annotated message 108 to a recipient. In at least one embodiment of the invention, the emotion metadata 106 is embedded in the message using standard extensible markup language (XML), by which additional information about an element is stored by providing an attribute that specifies the emotional classification of a message, such as, for example: "<emotional classification="angry">metadata information here</emotional classification>."

Additionally, components on the recipient side can extract this meta data (via meta data extraction module 116) and translate (that is, convert) the metadata (via emotion converter module 118) into a preferred or more obvious and/or understandable indication of the sender's emotional state (and present the same to the recipient via the emotion content display 122). In at least one embodiment of the invention, the emotion converter module 118 employs an XML parser (as part of metadata extraction module 116) to extract the emotion metadata and uses the metadata to parameterize a virtual avatar in the system of the recipient, which is then capable of expressing emotions in real-time. For example, if the recipient is of a different culture than the sender, that individual (the recipient) may desire or require additional aid in deciphering emotions of the sender. This aid can be rendered, for example, in the form of a conversion to a graphic, color, sound, animation, keywords, etc.

Additionally, note that in FIG. 1, the message itself can bypass meta data extraction module 116 because, for instance, the message constitutes the main body of the communication. Accordingly, the message can be presented immediately to the recipient as message output 120, much as in typical text messaging systems. The emotion converter module 118 can then augment this message output 120 with emotion content display module 122, which may, for example, include evolving, animated displays.

As noted, embedding and translation steps are carried out via the emotion converter module 118 which makes use of a machine-learning element to interpret: 1) the sender's emotional state, 2) the recipient user's current context based on the user profile 112 (and, optionally, a model of the user), and 3) the appropriate method and medium by which to represent the sender's emotional state to the recipient via emotion content display 122. The machine-learning element can receive instruction from the recipient, a caregiver or other third party or set of individuals, as well as from the sender in the form of subsequent training message 110 that is meant to notify the system that an emotional cue was not conveyed and/or represented appropriately to the recipient.

Note that the term model may refer to a dynamically updated user profile (such as profile 112) in which the state of the profile changes based on other profile parameters and/or a mathematical representation of how a profile parameter transitions from one state to another. Note also that receiver preferences 114 may be provided and updated manually by the recipient user in order to fine-tune or modify the emotion content display module 122. Such preferences 114 can also be inferred and/or derived from the user profile 112.

In connection with FIG. 1, at least one embodiment of the invention can be illustrated via the following example and description. A user composes an electronic communication containing message input 102. The electronic communication can include, for example, email, instant message, voice mail, communication in a virtual universe. animated communication, video, phone message, enriched form of tweet, and/or the forwarding of a message.

The user emotional state is detected (via emotional detection module 104) in the message input 102. Estimation of an emotional state can be performed via, for example, analyzing typing speed, typing errors, typing rhythm, biometrics, voice characteristics (in cases of voice mails), gesture recognition (in eases of video), biometrics of eye tracking, biometrics from a mouse movement to identify user emotions, etc. The system (for example, emotional detection module 104) extracts physiological and motor-behavioral measurements from mouse/keyboard/touch-screen actions and/or hand/gesture/voice characteristics, and the user may also input emotion data (self-reported), which can be used to analyze correlations with these other measurements. Such measurements can include, as noted, biometrics derived from a keyboard or touch-screen to identify user emotions, emotion biometrics detected with items used by users (such as, for example, a necklace), user behavior, past user communications, emails, phone calls, etc. Further, such measurements and the emotional states are amassed in a database, which is analyzed using standard statistical learning methods to find correlations and/or make predictions. These predictions may improve with time as more data are gathered and correlations are analyzed.

At least one embodiment of the invention can also include the use of a method that analyzes the rhythm of a person's typing. Such a method can include determining dwell times and flight times in the user communication in order to correlate typing rhythm with emotional states. A dwell time, as used herein, refers to the amount of time a key is pressed (keystroke down to keystroke up). Flight times, as used herein, represent the periods of time between one keystroke down and the next keystroke down, and one keystroke up and the next keystroke up, which produce a rhythm unique to the user when typing (such as, for example, when typing in a username and password which can be compared against future logins).

Additionally, at least one embodiment of the invention includes scanning a communication for certain keywords that indicate a particular emotional state of the user. Such a determination can be based, for example, on discovered and/or learned emotional states based on user feedback, including answers to questionnaires and/or psychological (for example, e-self-reports) data. Similarly, these keystroke data and emotional states are amassed in a database, which is analyzed using standard statistical learning methods to find correlations and/or make predictions. Further, the system can examine message context (recipient name, topic of email, location of recipient, etc.) in such determinations as well.

As also detailed herein, at least one embodiment of the invention includes deploying an action to reduce the likelihood of the user inappropriately sending a communication. Such an aspect can include warning the user about his or her emotional state, which can be carried out by the emotion detector module 104 in an example embodiment of the invention. The system may employ a warning in the form of an audio message, a tactile message, a speech message, a tone, an image, a lack of responsiveness in a communication device, a vibration, a chirp, a color change on a screen, a change in avatar appearance in a virtual world, a change of appearance of the environment in a virtual world, etc. The warning mechanism can make use of a multi-dimensional threshold (covering a range of emotional dimensions), parameterized by the user, by an employer, and/or automatically using parameters derived from a database. In a preferred embodiment of the invention, such a database provides data specific to the recipient and the expected reaction to certain emotions (for example, a culturally sensitive database of emotions and their expression).

At least one embodiment of the invention can additionally include determining an appropriate signature of a communication/message. Such a signature can be appended to the text body of the message and appear directly in message output 120, and/or can be embedded in the meta data 106. Automatically determining the signature of an email or other communication can be based, for example, on the following information: recipient, day, time of day, emotional state, holiday, topic of email, content of email, nature of recipient. (for example, within a company, a business, a newsgroup, a forum, gender, country, culture, etc.), learning from user feedback and recipient feedback on how to optimize content of a signature and appearance of a signature, social networks (for example, if a user is one degree away from another user in a social network), etc. At least one embodiment of the invention can make use of a mapping or look-up table derived from the emotion content of a message and the recipient data to form a set of possible salutations. For example, a salutation may be toggled by the system between the following options: 1) NO-CLOSING, 2) "Regards," 3) "Kind regards," 4) "Best regards," and 5) "Best," depending on the analysis performed.

Additionally, at least one embodiment of the invention includes attaching to the communication a standardized set of fields describing the emotional state of the user to create an annotated version of the message 108. The set of fields can include information to describe the emotional state of the user such as, for example, a text description of state, text formatting commands to be rendered by the recipient's email application, emoticons, animations, standard commands to control a remote device for emotion expression (for example, an "emotional robot"), etc. Similar to techniques detailed above, at least one embodiment of the invention can make use of a mapping or look-up table derived from the emotion content of a message and the recipient data to form a set of possible standardized field entries.

At least one embodiment of the invention can also include delaying the sending of a user communication by some determined amount of time that is a function of the emotional state of the user. Accordingly, during this delay, the user may opt to cancel sending of the communication, modify the contents of the communication message, etc. The amount of time a message is delayed may vary depending upon the moving average of a user's emotional state. The risk of a miscommunication may be evaluated based on the content of the message, and as a threshold is approached, the delays can grow longer. Additionally, in conjunction with delaying the sending of a user communication, at least one embodiment of the invention can include providing a signal to the sender that the communication in question has been assigned to any of the following: a queue, a calendar storage component, a password protected storage component, etc. Further, at least one embodiment of the invention can include prompting the user (sender) to determine and/or further modify a delay by way of a follow-up interview/questionnaire, additional observation of the user's emotional state, and/or automated mediation between the sender and recipient (for example, via other communication observed by the system).

At least one embodiment of the invention can additionally include redirecting the communication in question to a designated reviewer (for example, a trusted individual, caregiver or manager) based on the emotional state of the sender. The designated review can be performed by someone who is pre-selected/pre-identified by the user, and whose contact information is stored within the system for this purpose. Such an embodiment can include automatically forwarding the message to the designated review with an alert that a review and/or automated mediation between the sender and the reviewer is required.

Figure 2:
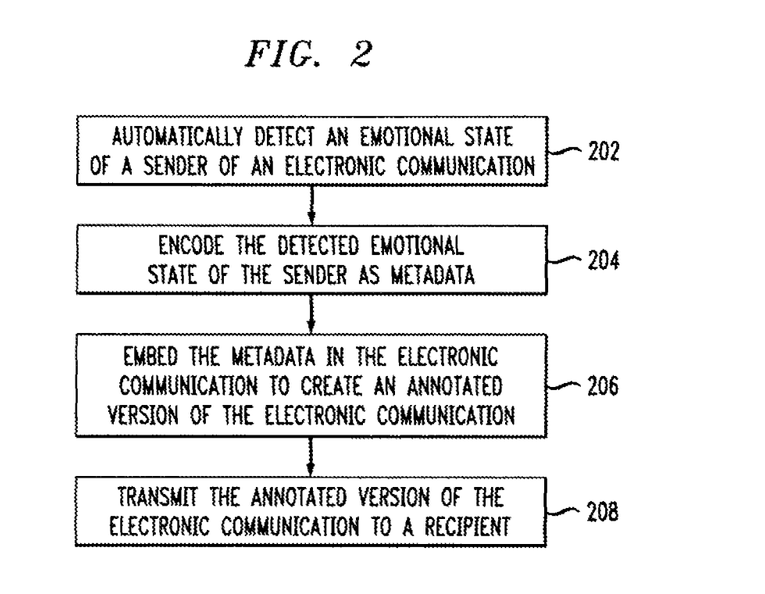
FIG. 2 is a flow diagram illustrating techniques for transmitting an electronic communication in annotated form based on a detected emotional state of a sender of the electronic communication, according to an embodiment of the invention.

FIG. 2 is a flow diagram illustrating techniques for transmitting an electronic communication in annotated form based on a detected emotional state of a sender of the electronic communication, according to an embodiment of the present invention. Step 202 includes automatically detecting an emotional state of a sender of an electronic communication. As noted herein, the electronic communication can include an email, an instant message, a voice mail, a communication in a virtual universe, an animated communication, a video segment, a text message, a tweet, and/or a forwarding of a separate message.

Automatically detecting an emotional state of a sender can include determining physiological parameters and/or motor-behavioral parameters based on sender action.

Additionally, at least one embodiment of the invention includes analyzing sender typing speed, sender typing errors, sender typing rhythm, sender biometrics derived from eye tracking, biometrics derived from engagement of a mouse, pointer or touch-screen of a sender device, sender voice characteristic and/or gesture recognition of the sender. Further, as detailed herein, automatically detecting an emotional state of a sender can include scanning the electronic communication to identify one or more keywords that indicate a particular emotional state of the sender. Such an identification can be based on discovered and/or learned emotional states derived in connection with user feedback.

Step 204 includes encoding the detected emotional state of the sender, using input from at least one additional source, as metadata. Step 206 includes embedding the metadata in the electronic communication to create an annotated version of the electronic communication.

Step 208 includes transmitting the annotated version of the electronic communication to a recipient. The transmitting can be carried out, for example, in accordance with at least one pre-determined recipient preference (such as, for example, receiving the annotated version of the electronic communication in computer graphic form and/or in audio form, providing an emphasis on sender's emotional state in the annotated version of the electronic communication, etc.).

The techniques depicted in FIG. 2 can also include extracting the metadata from the annotated version of the electronic communication, and converting the metadata into a representation of the emotional state of the sender to present to the recipient with the annotated version of the electronic communication. The representation of the emotional state can be in a form of, for example, a graphic, a color change, an animation. a sound, and/or at least one keyword. Additionally, converting can include implementing a machine-learning element to interpret a context of the recipient based on a user profile of the recipient. The machine-learning element can further incorporate input from the recipient and/or a third party, as well as input from the sender, recipient, and/or third party in the form of a subsequent training to provide notification that an emotional state was not represented appropriately to the recipient.

Further, at least one embodiment of the invention includes providing the sender with a notification of the detected emotional state. The notification can include, for example, an audio message, a tactile message, a speech message, a tone, an image, a lack of responsiveness in a communication device, a vibration, a color change on a screen, a change in avatar appearance in a virtual world, and/or a change of appearance of an environment in a virtual world. The techniques depicted in FIG. 2 can also include delaying the transmission of the annotated version of the electronic communication by a pre-determined amount of time that is a function of the detected emotional state of the sender. Additionally, at least one embodiment of the invention includes redirecting the electronic communication to a designated reviewer based on the detected emotional state of the sender.

Also, as described herein, an aspect of the invention includes automatically managing a transmission of an electronic communication based on an emotional state of a sender of the electronic communication. Accordingly, at least one embodiment of the invention includes automatically detecting an emotional state of an author of an electronic communication, providing the author with a notification of the detected emotional state, delaying transmission of the electronic communication to a recipient by a pre-determined amount of time that is a function of the detected emotional state of the author, and deploying an action to facilitate modification and/or cancellation of the transmission of the electronic communication during said delay.

The techniques depicted in FIG. 2 can also, as described herein, include providing a system, wherein the system includes distinct software modules, each of the distinct software modules being embodied on a tangible computer-readable recordable storage medium. All of the modules (or any subset thereof) can be on the same medium, or each can be on a different medium, for example. The modules can include any or all of the components shown in the figures and/or described herein. In an aspect of the invention, the modules can run, for example, on a hardware processor. The method steps can then be carried out using the distinct software modules of the system, as described above, executing on a hardware processor. Further, a computer program product can include a tangible computer-readable recordable storage medium with code adapted to be executed to carry out at least one method step described herein, including the provision of the system with the distinct software modules.

Additionally, the techniques depicted in FIG. 2 can be implemented via a computer program product that can include computer useable program code that is stored in a computer readable storage medium in a data processing system, and wherein the computer useable program code was downloaded over a network from a remote data processing system. Also, in an aspect of the invention, the computer program product can include computer useable program code that is stored in a computer readable storage medium in a server data processing system, and wherein the computer useable program code is downloaded over a network to a remote data processing system for use in a computer readable storage medium with the remote system.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in a computer readable medium having computer readable program code embodied thereon.

An aspect of the invention or elements thereof can be implemented in the form of an apparatus including a memory and at least one processor that is coupled to the memory and operative to perform exemplary method steps.

Figure 3:
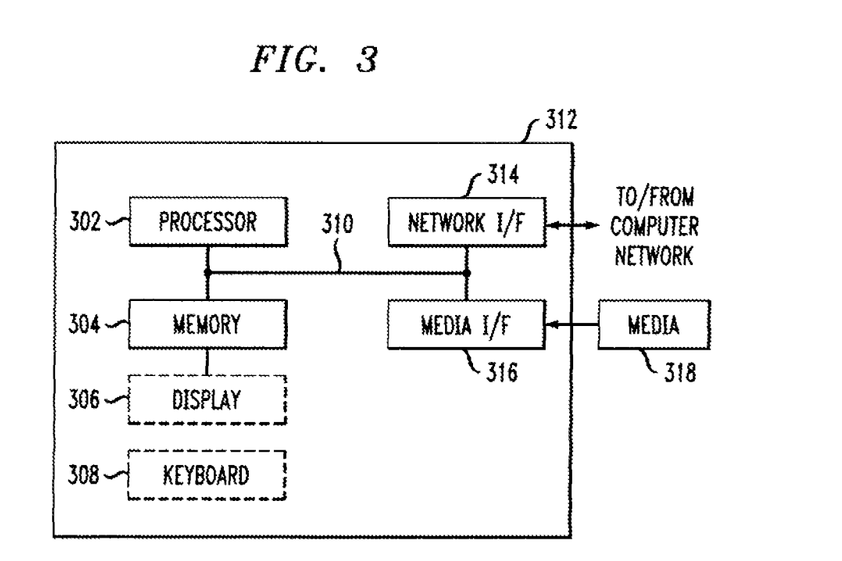
FIG. 3 is a system diagram of an exemplary computer system on which at least one embodiment of the invention can be implemented.

Additionally, an aspect of the present invention can make use of software miming on a general purpose computer or workstation. With reference to FIG. 3, such an implementation might employ, for example, a processor 302, a memory 304, and an input/output interface formed, for example, by a display 306 and a keyboard 308. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory), ROM (read only memory), a fixed memory device (for example, hard drive), a removable memory device (for example, diskette), a flash memory and the like. In addition, the phrase "input/output interface" as used herein, is intended to include, for example, a mechanism for inputting data to the processing unit (for example, mouse), and a mechanism for providing results associated with the processing unit (for example, printer). The processor 302, memory 304, and input/output interface such as display 306 and keyboard 308 can be interconnected, for example, via bus 310 as part of a data processing unit 312. Suitable interconnections, for example via bus 310, can also be provided to a network interface 314, such as a network card, which can be provided to interface with a computer network, and to a media interface 316, such as a diskette or CD-ROM drive, which can be provided to interface with media 318.

Accordingly, computer software including instructions or code for performing the methodologies of the invention, as described herein, may be stored in associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

A data processing system suitable for storing and/or executing program code will include at least one processor 302 coupled directly or indirectly to memory elements 304 through a system bus 310. The memory elements can include local memory employed during actual implementation of the program code, bulk storage, and cache memories which provide temporary storage of at least some program code in order to reduce the number of times code must be retrieved from bulk storage during implementation.

Input/output or I/O devices (including but not limited to keyboards 308, displays 306, pointing devices, and the like) can be coupled to the system either directly (such as via bus 310) or through intervening I/O controllers (omitted for clarity).

Network adapters such as network interface 314 may also be coupled to the system to enable the data processing system to become coupled to other data processing systems or remote printers or storage devices through intervening private or public networks. Modems, cable modem and Ethernet cards are just a few of the currently available types of network adapters.

As used herein, including the claims, a "server" includes a physical data processing system (for example, system 312 as shown in FIG. 3) running a server program. It will be understood that such a physical server may or may not include a display and keyboard.

As noted, aspects of the present invention may take the form of a computer program product embodied in a computer readable medium having computer readable program code embodied thereon. Also, any combination of computer readable media may be utilized. The computer readable medium may be a computer readable signal medium or a computer readable storage medium, A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using an appropriate medium, including but not limited to wireless, wireline, optical fiber cable, RF, etc., or any suitable combination of the foregoing.

Computer program code for carrying out operations for aspects of the present invention may be written in any combination of at least one programming language, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. Accordingly, an aspect of the invention includes an article of manufacture tangibly embodying computer readable instructions which, when implemented, cause a computer to carry out a plurality of method steps as described herein.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods and computer program products according to various embodiments of the present invention. In this regard, each block in the flowchart or block diagrams may represent a module, component, segment, or portion of code, which comprises at least one executable instruction for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

It should be noted that any of the methods described herein can include an additional step of providing a system comprising distinct software modules embodied on a computer readable storage medium; the modules can include, for example, any or all of the components detailed herein. The method steps can then be carried out using the distinct software modules and/or sub-modules of the system, as described above, executing on a hardware processor 302. Further, a computer program product can include a computer-readable storage medium with code adapted to be implemented to carry out at least one method step described herein, including the provision of the system with the distinct software modules.

In any case, it should be understood that the components illustrated herein may be implemented in various forms of hardware, software, or combinations thereof, for example, application specific integrated circuit(s) (ASICS), functional circuitry, an appropriately programmed general purpose digital computer with associated memory, and the like. Given the teachings of the invention provided herein, one of ordinary skill in the related art will be able to contemplate other implementations of the components of the invention.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of another feature, integer, step, operation, element, component, and/or group thereof.

The corresponding structures, materials, acts, and equivalents of all means or step plus function elements in the claims below are intended to include any structure, material, or act for performing the function in combination with other claimed elements as specifically claimed.

At least one aspect of the present invention may provide a beneficial effect such as, for example, translation of message metadata into a more obvious and/or understandable indication of the message sender's emotional intent.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. An article of manufacture comprising a non-transitory computer readable storage medium having computer readable instructions tangibly embodied thereon which, when implemented, cause a computer to carry out a plurality of method steps comprising:
   automatically detecting an emotional state of a sender of an electronic communication wherein said automatically detecting comprises:
   analyzing sender biometrics comprising one or more physiological measurements and/or one or more motor-behavioral measurements derived from engagement with a keyboard, a pointer and/or a touch-screen of a sender device used by the sender to generate the electronic communication; and
   correlating, via a hardware processor, said sender biometrics with multiple biometric measurements amassed in a database using one or more statistical learning methods, wherein the multiple biometric measurements amassed in the database correspond to one or more emotional states;
   encoding the detected emotional state of the sender, using input from at least one additional source, as metadata;
   embedding the metadata in the electronic communication to create an annotated version of the electronic communication;
   delaying transmission of the annotated version of the electronic communication to a recipient by a pre-determined amount of time that is a function of: (i) a moving average of the detected emotional state of the sender computed over a given interval of time and (ii) an evaluated amount of a risk of miscommunication, evaluated based on content of the electronic communication, in relation to a given risk of communication threshold;
   redirecting, during the pre-determined amount of time associated with said delaying, (i) the annotated version of the electronic communication to a designated third party reviewer and (ii) an alert to the designated third party reviewer that a review and/or an automated mediation between the sender and the designated third party reviewer is required, wherein said redirecting is based on the detected emotional state of the sender, and wherein the designated third party reviewer comprises at least one of (a) a caregiver of the sender, (b) a manager of the sender, and (c) an individual identified as trusted by the sender;
   providing a signal to the sender in connection with said delaying, wherein said signal comprises:
      a notification of said delaying of the transmission of the annotated version of the electronic communication to the recipient; and
      a prompt enabling the sender to modify the pre-determined amount of time of said delaying via one or more mechanisms;
   extracting the metadata from the annotated version of the electronic communication of the recipient;
   converting the metadata into a representation of the detected emotional state of the sender to present to the recipient with the annotated version of the electronic communication, wherein said converting comprises implementing a machine-learning element to interpret a context of the recipient based on the detected emotional state of the sender, and in accordance with one or more user attributes derived from a user profile of the recipient; and
   transmitting, subsequent to (a) said delaying by the pre-determined amount of time and (b) said redirecting, (i) the representation of the emotional state of the sender and (ii) the annotated version of the electronic communication to the recipient in accordance with at least one pre-determined preference specified by the recipient in a recipient profile.

2. The article of manufacture of claim 1, wherein the electronic communication comprises an email, an instant message, a voice mail, a communication in a virtual universe, an animated communication, a video segment, a text message, a tweet, and/or a forwarding of a separate message.

3. The article of manufacture of claim 1, wherein the at least one pre-determined recipient preference comprises receiving the annotated version of the electronic communication in computer graphic form and/or in audio form.

4. The article of manufacture of claim 1, wherein the representation of the detected emotional state of the sender is in a form of a graphic, a color change, an animation, a sound, and/or at least one keyword.

5. The article of manufacture of claim 1, wherein the method steps comprise:
receiving input from the sender, recipient, and/or third party in a form of a subsequent training to provide notification that the emotional state was not represented appropriately to the recipient.

6. The article of manufacture of claim 1, wherein said automatically detecting the emotional state of the sender comprises analyzing at least one of sender typing speed, sender typing errors, and sender typing rhythm.

7. The article of manufacture of claim 1, wherein said automatically detecting the emotional state of the sender comprises analyzing sender biometrics derived from eye tracking.

8. The article of manufacture of claim 1, wherein said automatically detecting the emotional state of the sender comprises analyzing a sender voice characteristic.

9. The article of manufacture of claim 1, wherein the method steps comprise:
providing the sender with a notification of the detected emotional state, wherein the notification comprises at least one of an audio message, a tactile message, a speech message, a tone, an image, a lack of responsiveness in a communication device, a vibration, a color change on a screen, a change in avatar appearance in a virtual world, and a change of appearance of an environment in a virtual world.

10. The article of manufacture of claim 1, wherein said automatically detecting the emotional state of the sender comprises analyzing gesture recognition of the sender.

11. The article of manufacture of claim 1, wherein said automatically detecting the emotional state of the sender comprises scanning the electronic communication to identify one or more keywords that indicate a particular emotional state of the sender.

12. The article of manufacture of claim 11, wherein said identifying one or more keywords that indicate a particular emotional state is based on discovered and/or learned emotional states derived in connection with user feedback.

13. A system for exchanging an electronic communication in annotated form based on a detected emotional state of a sender of the electronic communication, comprising:
a memory; and
at least one processor coupled to the memory and operative for:
automatically detecting an emotional state of the sender of the electronic communication wherein said automatically detecting comprises:
analyzing sender biometrics comprising one or more physiological measurements and/or one or more motor-behavioral measurements derived from engagement with a keyboard, a pointer and/or a touch-screen of a sender device used by the sender to generate the electronic communication; and
correlating, via a hardware processor, said sender biometrics with multiple biometric measurements amassed in a database using one or more statistical learning methods, wherein the multiple biometric measurements amassed in the database correspond to one or more emotional states;
encoding the detected emotional state of the sender, using input from at least one additional source, as metadata;
embedding the metadata in the electronic communication to create an annotated version of the electronic communication;
delaying transmission of the annotated version of the electronic communication to a recipient by a pre-determined amount of time that is a function of: (i) a moving average of the detected emotional state of the sender computed over a given interval of time and (ii) an evaluated amount of a risk of miscommunication, evaluated based on content of the electronic communication, in relation to a given risk of communication threshold;
redirecting, during the pre-determined amount of time associated with said delaying, (i) the annotated version of the electronic communication to a designated third party reviewer and (ii) an alert to the designated third party reviewer that a review and/or an automated mediation between the sender and the designated third party reviewer is required, wherein said redirecting is based on the detected emotional state of the sender, and wherein the designated third party reviewer comprises at least one of (a) a caregiver of the sender, (b) a manager of the sender, and (c) an individual identified as trusted by the sender;
providing a signal to the sender in connection with said delaying, wherein said signal comprises:
a notification of said delaying of the transmission of the annotated version of the electronic communication to the recipient; and
a prompt enabling the sender to modify the pre-determined amount of time of said delaying via one or more mechanisms;
extracting the metadata from the annotated version of the electronic communication of the recipient;
converting the metadata into a representation of the detected emotional state of the sender to present to the recipient with the annotated version of the electronic communication, wherein said converting comprises implementing a machine-learning element to interpret a context of the recipient based on the detected emotional state of the sender, and in accordance with one or more user attributes derived from a user profile of the recipient; and
transmitting, subsequent to (a) said delaying by the pre-determined amount of time, and (b) said redirecting, (i) the representation of the emotional state of the sender and (ii) the annotated version of the electronic communication to the recipient in accordance with at least one pre-determined preference specified by the recipient in a recipient profile.

14. An article of manufacture for automatically managing a transmission of an electronic communication based on an emotional state of a sender of the electronic communication, comprising a non-transitory computer readable storage medium having computer readable instructions tangibly embodied thereon which, when implemented, cause a computer to carry out a plurality of method steps comprising:
automatically detecting an emotional state of the sender of the electronic communication wherein said automatically detecting comprises:
analyzing sender biometrics comprising one or more physiological measurements and/or one or more motor-behavioral measurements derived from engagement with a keyboard, a pointer and/or a touch-screen of a sender device used by the sender to generate the electronic communication;

correlating, via a hardware processor, said sender biometrics with multiple biometric measurements amassed in a database, wherein the multiple biometric measurements amassed in the database using one or more statistical learning methods, correspond to one or more emotional states;

generating a representation of the detected emotional state of the sender to present to a given recipient with the annotated version of the electronic communication, wherein said generating comprises implementing a machine-learning element to interpret a context of the given recipient based on the detected emotional state of the sender, and in accordance with one or more user attributes derived from a user profile of the given recipient;

providing the sender of the electronic communication with a notification of the detected emotional state of the sender;

delaying transmission of the electronic communication to the given recipient by a pre-determined amount of time that is a function of: (i) a moving average of the detected emotional state of the sender computed over a given interval of time and (ii) an evaluated amount of a risk of miscommunication, evaluated based on content of the electronic communication, in relation to a given risk of communication threshold;

providing a signal to the sender in connection with said delaying, wherein said signal comprises:
   a notification of said delaying of the transmission of the an electronic communication to the recipient; and
   a prompt enabling the sender to modify the pre-determined amount of time of said delaying via one or more mechanisms; and deploying an action to facilitate modification and/or cancellation of the transmission of the electronic communication during said delaying, wherein said action comprises redirecting (i) the electronic communication to a designated third party reviewer and (ii) an alert to the designated third party reviewer that a review and/or an automated mediation between the sender and the designated third party reviewer is required, wherein said redirecting is based on the detected emotional state of the sender, and wherein the designated third party reviewer comprises at least one of (a) a caregiver of the sender, (b) a manager of the sender, and (c) an individual identified as trusted by the sender.

15. The article of manufacture of claim 14, wherein the notification comprises at least one of an audio message, a tactile message, a speech message, a tone, an image, a lack of responsiveness in a communication device, a vibration, a color change on a screen, a change in avatar appearance in a virtual world, and a change of appearance of an environment in a virtual world.

* * * * *